United States Patent [19]

Ho et al.

[11] 4,423,623
[45] Jan. 3, 1984

[54] MICROWAVE METER FOR FLUID MIXTURES

[75] Inventors: William W. Ho; Alan B. Harker; Ira B. Goldberg; Kwang E. Chung, all of Thousand Oaks, Calif.

[73] Assignee: Rockwell International Corporation, El Segundo, Calif.

[21] Appl. No.: 295,904

[22] Filed: Aug. 24, 1981

[51] Int. Cl.³ .......................... G01N 22/00; G01F 1/70
[52] U.S. Cl. .................................. 73/61 R; 73/861.06; 324/58.5 A
[58] Field of Search .................. 73/73, 861.04, 861.06, 73/861.08, 61 R; 324/58 A, 58.5 R, 58.5 A, 58.5 C

[56] References Cited

U.S. PATENT DOCUMENTS

| | | | |
|---|---|---|---|
| 2,463,297 | 3/1949 | Muskat et al. | 324/58.5 A |
| 2,703,079 | 3/1955 | Argento | 324/58.5 A X |
| 2,982,855 | 5/1961 | Wickersham | 324/58.5 A X |
| 3,103,627 | 9/1963 | Schneider | 324/58.5 A |
| 3,373,357 | 3/1968 | Keenan et al. | 324/58.5 A |
| 3,762,221 | 10/1973 | Coulthard | 73/861.06 |
| 3,939,406 | 2/1976 | Billeter et al. | 324/58.5 C |
| 3,952,246 | 4/1976 | Sprott et al. | 324/58.5 A |
| 3,956,695 | 5/1976 | Stamm | 324/58.5 A |

FOREIGN PATENT DOCUMENTS 607133  5/1978  U.S.S.R. ...................... 324/58.5 A

OTHER PUBLICATIONS

D. A. Ellerbruch–"Microwave Methods for Cryogenic Liquid & Slush Instrumentation", IEEE Trans. on Inst. and Meas., vol. IM-19, No. 4, Nov. 1970, pp. 412–416.
D. W. Griffen, "Development in Microwave Instrumentation for Ind. Process Control", Elec. Instrumentation Conf., May 1972, pp. 180–185.

Primary Examiner—Charles A. Ruehl
Attorney, Agent, or Firm—H. Fredrick Hamann; Craig O. Malin

[57] ABSTRACT

A meter and a method are provided for measuring the composition and flow rate of a coal slurry and other similar mixtures. The meter is a waveguide through which the mixture flows. Microwaves are propagated in the waveguide from a transmitter probe. A detector probe spaced from the transmitter probe receives signals from the microwaves. Those signals are processed to determine a characteristic frequency of the waveguide or the wavelength of the propagating microwave, which are related to the composition of the mixture within the waveguide. A second transmitter and detector pair determines these properties for another portion of the waveguide. Differences in the frequencies resulting from inhomogenuities in the mixture are cross correlated to determine the flow rate of the mixture.

11 Claims, 7 Drawing Figures

MICROWAVE METER FOR FLUID MIXTURES

BACKGROUND OF THE INVENTION

This invention relates to the field of meters and particularly to meters for measuring the composition and flow rate of fluid mixtures.

In order to control processes which utilize fluid mixtures of two materials, continuous or rapid monitoring of the composition of the mixture and its flow rate is highly desirable. One specific system which requires the measurement of mass-flow rate is the coal-water slurry transport system used in coal gasification processes, long range transport, and other industrial energy applications.

Because of the nature of coal slurry mixtures, most conventional measurement techniques are not applicable. The erosive nature of the flowing media precludes the use of devices which have moving parts or fragile components which must be immersed into the flow stream, or measurement surfaces adjacent to the flow. For measurements requiring pressure transmission through fine openings or flow through small by-pass tubes, clogging caused by the solid coal particles, perturbation of the main flow, and sampling present difficult problems.

At present, direct sampling and weighing techniques are used as reliable primary methods for determining material concentration and flow rate. The measurements require up to several hours and are impractical for continuous monitoring, although they are useful for calibrating other measuring devices.

Microwave techniques have been used for detecting variations in the composition (particularly variations in moisture) of materials. U.S. Pat. No. 3,818,333 describes a method which utilizes the attenuation of microwave power by water in a moist particulate material to determine the moisture content of the particulate material. Similarly, U.S. Pat. No. 3,783,373 describes the use of microwaves for monitoring the density of a rod of tobacco based upon the attenuation of the radiation caused by the presence of the rod of tobacco.

The change in resonance of a resonant microwave chamber has also been used to monitor the composition of a substance in the chamber. According to U.S. Pat. No. 3,586,971, variations in the dielectric characteristics of a substance can be determined by measuring the slow wave resonance shift of material placed in a slow wave structure. According to U.S. Pat. No. 3,612,996, the water content in butter can be determined by measuring the resonant frequency of a resonant microwave chamber containing the butter.

SUMMARY OF THE INVENTION

It is an object of the invention to provide a meter for measuring the composition of a fluid mixture.

It is an object of the invention to provide a meter for measuring the flow rate of a heterogeneous fluid mixture.

It is an object of the invention to provide a meter for measuring both the composition and flow rate of a heterogeneous fluid mixture.

It is an object of the invention to provide a meter for measuring the coal content of a coal slurry.

It is an object of the invention to provide a meter for measuring the flow rate of a coal slurry.

According to the invention, a section of the pipe serves as a waveguide which is positionable in series in the path of a flowing mixture such as powdered coal in water (coal slurry). There are two microwave probes in the waveguide, a transmitter probe for introducing microwave energy into the waveguide and a detector or receiver probe for extracting signals from the microwaves after they have traveled down the waveguide.

A microwave generator provides microwave energy for the transmitter probe; a portion of the power propagating in the pipe is received at the detector probe and amplified, rectified, and sent to a lock-in amplifier to determine a characteristic frequency of microwave propagation within the waveguide. Such a characteristic frequency can be a frequency corresponding to the guide wavelength, $\lambda_g$, of a wave propagating in the waveguide, the cut-off wavelength of the waveguide, or the frequency at which either the maximum signal or the minimum signal is observed at the receiver probe.

These characteristic frequencies depend upon the dielectric constant of the mixture filling the waveguide between the transmitter and receiver probes. The dielectric constant, in turn, depends upon the concentration (volume fraction) of the ingredients (such as coal and water) in the mixture. Thus, a relationship between the composition of the mixture and a characteristic frequency in the waveguide or the wavelength of the propagating wave can be obtained. These relationships are used by the meter for measuring the composition of the mixture.

To determine the flow rate of the mixture, a second pair of transmitter and detector probes is positioned in the waveguide at a predetermined distance from the first set of probes. This second set of probes also has the electronics necessary to determine a frequency characteristic of microwave propagation within the waveguide between its probes. Because of local variations in the composition of heterogeneous mixtures such as coal slurries, there are time dependent fluctuations in the characteristic frequency observed by either pair of probes. By using a lock-in amplifier, the frequency can be followed as the composition changes, so that the frequency can be translated into a voltage. Thus, fluctuations are monitored at two different locations along the waveguide. This permits, for example, a maximum signal from the upstream probes to be related to the same maximum signal at the downstream probes at a later time. The time difference obtained by this cross correlation is directly related to the velocity of the mixture.

These and other objects and features of the invention will be apparent from the following description, taken with reference to the accompanying drawings.

DESCRIPTION OF THE PREFERRED EMBODIMENT

Figure 1:
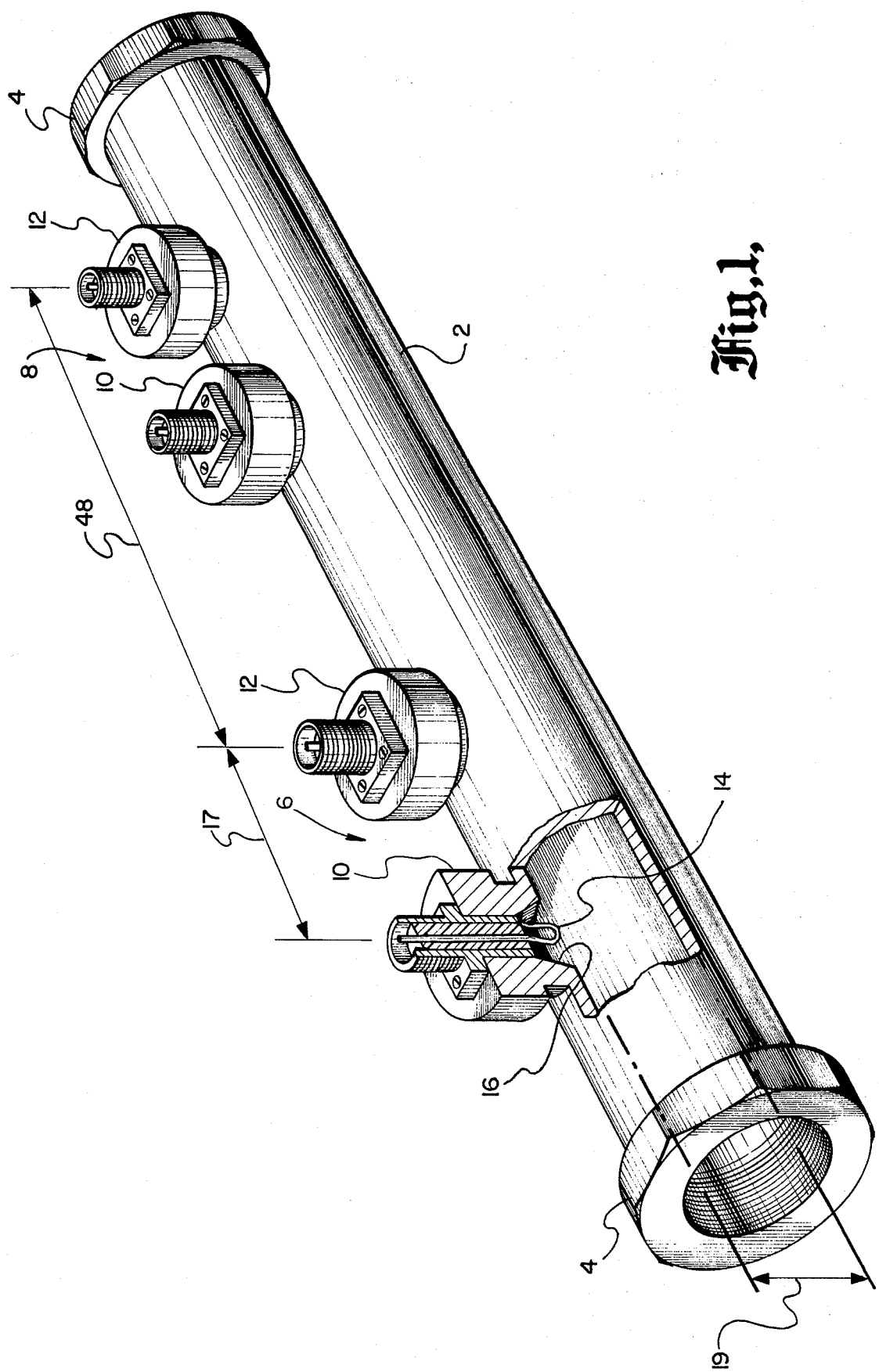
FIG. 1 is a perspective view of the meter without its associated electronics.

FIG. 1 is a perspective view of the meter without its associated electronics. It is a waveguide 2 having threaded couplings or flange 4 to join it in series with a conduit through which the mixture flows. Waveguide 2 thus becomes part of the conduit which is filled with the mixture and can be the same internal diameter as the adjacent pipe to avoid flow restrictions.

As shown in FIG. 1, the meter has a transmitter microwave probe 10 and a detector microwave probe 12. As shown in the cutaway portion of probe 10, a loop antenna 14 is used to couple microwaves into the waveguide. This coupling loop is located in a recess 16 in the waveguide wall so as to be protected from the flow of the mixture. The microwave transmitter probe 10 is separated from the microwave detector probe 12 by a predetermined distance 17. Microwaves are coupled into waveguide 2 through transmitter probe 10, and after they have traveled distance 17 their signal is picked up by detector probe 12.

Thus, the meter is a dielectric-filled waveguide. By measuring the frequency of microwave propagation within the waveguide, the real part of the dielectric constant of the mixture filling the waveguide can be directly determined. For a circular waveguide such as shown in FIG. 1, the frequency and guide wavelength for the $TM_{01}$ mode of microwave propagation in the waveguide is related to the guide wavelength by the dielectric constant as shown by the equation:

$$\epsilon' = \frac{c^2}{f^2}\left[\frac{1}{\lambda_g^2} + \frac{0.3436}{D^2}\right], \quad (1)$$

where:
$\epsilon'$ = the dielectric constant of the mixture,
c = the speed of light in a vacuum,
f = the frequency,
$\lambda_g$ = the wavelength (equal to distance 17 in the meter)
D = the diameter 19 of the circular waveguide.

For the meter shown in FIG. 1, $\lambda_g$ and D are established values which depend upon the mode of microwave propagation. Consequently, by measuring the frequency at which a microwave of length $\lambda_g$ propagates in the waveguide, the value of the dielectric constant, $\epsilon$, of the mixture can be determined. This value of $\epsilon$ can be approximately related to the fraction of ingredients in the mixture by calculation using the Maxwell-Garnet, Looyenga, or some other equation. Alternatively, the characteristic frequency can be empirically related to the composition of the mixture. The frequency, f, can be determined by varying the input frequency at transmitting probe 10 and observing the resulting signal at receiver probe 12. In a first embodiment of this invention, the method of measurement is to monitor the frequency at which the signal is at a minimum so that the wavelength in the waveguide is an even multiple of distance 17 between the two probes.

Figure 2:
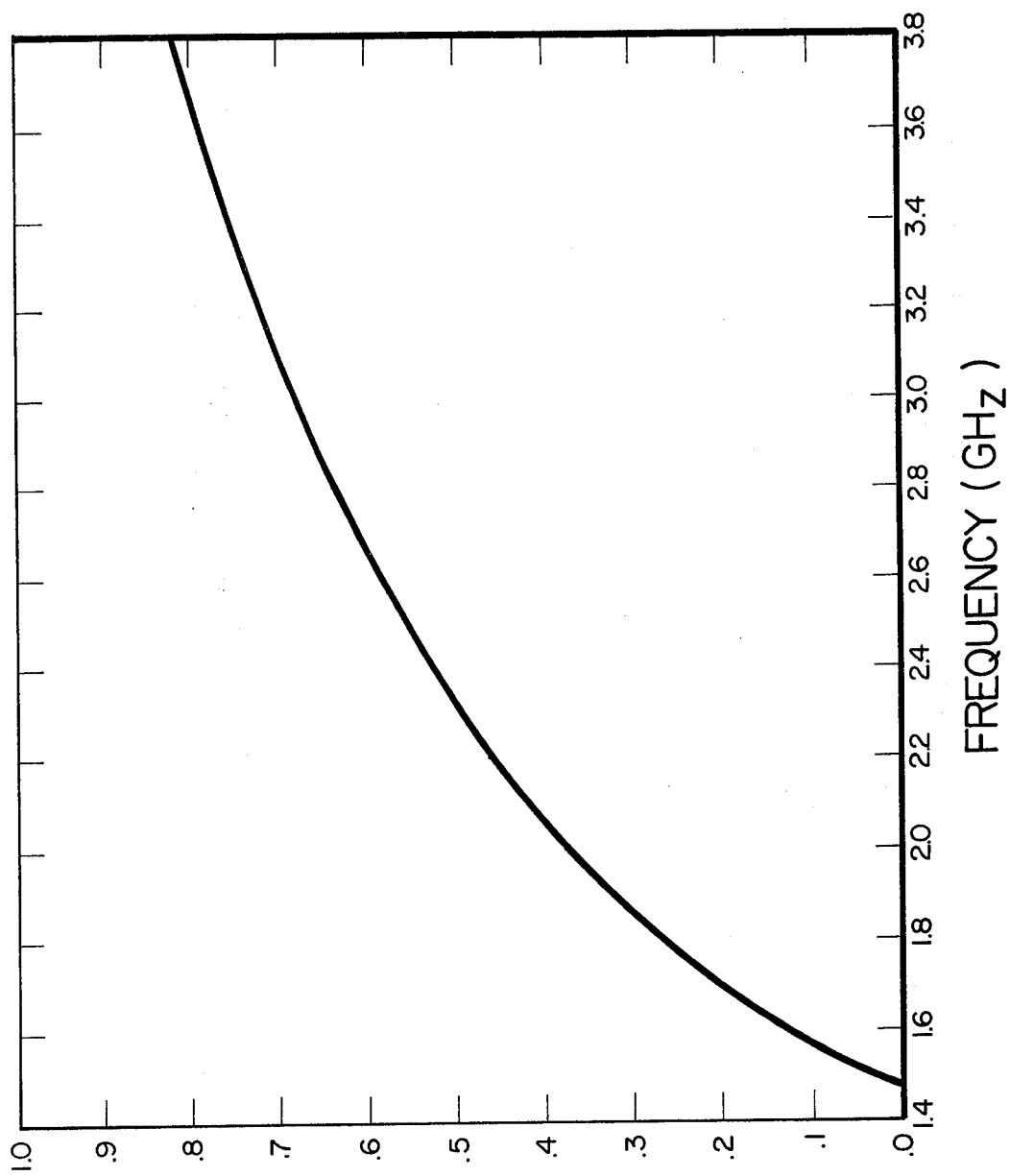
FIG. 2 is a graph showing the relationship between frequency and the fraction of coal in a slurry as calculated using equations 1 and 2 for a ¾inch diameter waveguide for $\lambda_g = 3.57$ cm and the known density of coal and water.

FIG. 2 shows a relationship between frequency, f, and volume fraction $\phi$ of coal in a mixture of coal powder and water (a coal slurry). The volume fraction shown in FIG. 2 was calculated for a ¾ inch diameter pipe (D=¾ inch) with a separation of 3.57 cm between the probes ($\lambda_g$=3.57 cm), using Equation 1 and the following Looyenga expression:

$$\bar{\epsilon}' = [(\epsilon'_i{}^{\frac{1}{3}} - \epsilon'_m{}^{\frac{1}{3}})\phi_i + \epsilon'_i{}^{\frac{1}{3}}]^3 \quad (2)$$

where:
$\epsilon'_i$ = the dielectric constant of the particles (coal for example),
$\epsilon'_m$ = the dielectric constant of the liquid (water for example),
$\phi_i$ = the volume fraction of the particles in the liquid, and
$\epsilon'$ = the dielectric constant of the mixture.

For practical applications where high accuracy is required, experimental measurements are used to establish the exact relationship between the fraction of ingredients in the mixture and the characteristic frequency for the particular meter.

Figure 3:
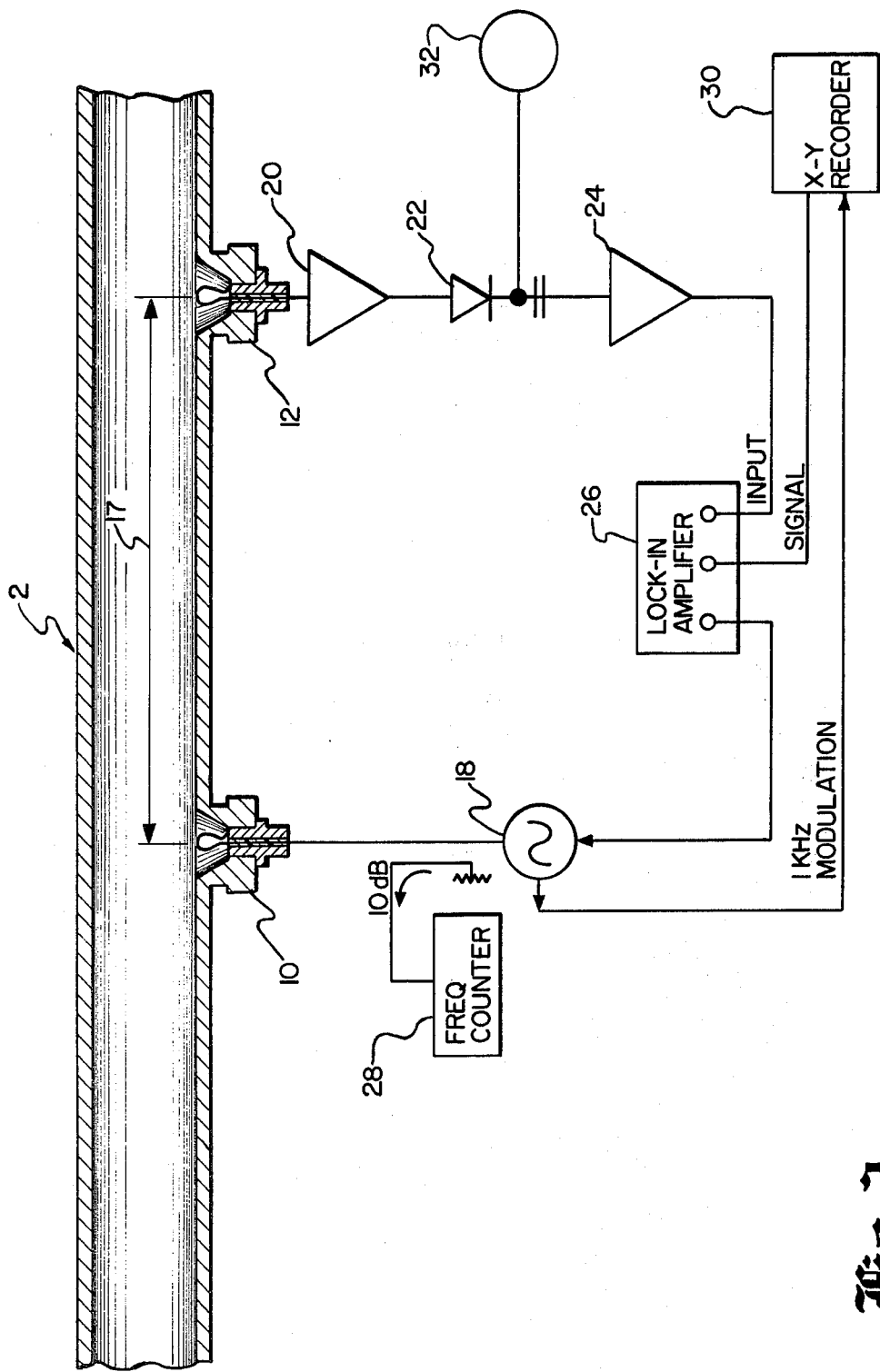
FIG. 3 is a schematic of the microwave system and detector and transmitter electronics used in the meter.

FIG. 3 shows the microwave system and detector electronics which are used to measure the excitation frequency of the waveguide. Microwave power is fed into the waveguide via a coupling loop recessed into a fitting placed on the waveguide. This fitting provides a static area in which there is no slurry flow, so that the coupling loop will neither interfere with the slurry flow nor be damaged by it. The distance 17 between transmitting probe 10 and detecting probe 12 is based upon the expected attenuation of microwave power by the mixture in the waveguide.

Examples of microwave sources 18 are a Texscan Model VS-90B sweep generator, a Wavetek Model 2002A generator, or a voltage controlled oscillator. These sources can permit or can be modified to permit frequency modulation while set to a constant frequency or while being swept by internal controls.

The signal obtained from detector probe 12 can be amplified by low noise amplifier 20 and is fed to a broadband detector 22. The rectified signal from detector 22 is fed into operational amplifier 24 and then into lock-in amplifier 26, so that a low noise signal can be obtained. The lock-in amplifier can be used to detect the signal (or its derivatives) as a function of the modulation frequency, or it can be fixed at a desired frequency.

For detection of the power in detector probe 12, amplitude modulation of the sweep generator is used. In order to determine the derivative, frequency modulation is used. The microwave frequency is calibrated using frequency counter 28. Output from lock-in amplifier 26 can be monitored by x-y recorder 30, oscilloscope 32, or suitable voltmeter.

Thus, in the above-described first embodiment of the invention, the frequency of the minimum signal of a propagating microwave is used as an indication of the fraction of ingredients in the mixture. In a second embodiment of the invention, the cut-off frequency of the propagating microwave, or a frequency in which the maximum power is observed at the receiver, is used as an indication of the fraction of ingredients in the mixture. In actual tests of the two embodiments it was found that the embodiment in which the frequency corresponds to the maximum signal at the detector gave better resolution than the first embodiment. This frequency is very close to the cut-off frequency.

The cut-off frequency is defined as the minimum frequency at which microwaves of a given mode of propagation are transmitted through a lossless waveguide.

The cut-off frequency, $f_c$, is dependent upon the dielectric constant of the medium in the waveguide according to the relation:

$$f_c = C/\lambda_c(\epsilon')^{\frac{1}{2}} \qquad (3)$$

The value of $\epsilon'$ depends upon the composition of the medium in the waveguide. Thus, the waveguide can be used as a meter if it is calibrated empirically to relate the cut-off frequency to the composition of the fluid in the waveguide.

Figure 4:
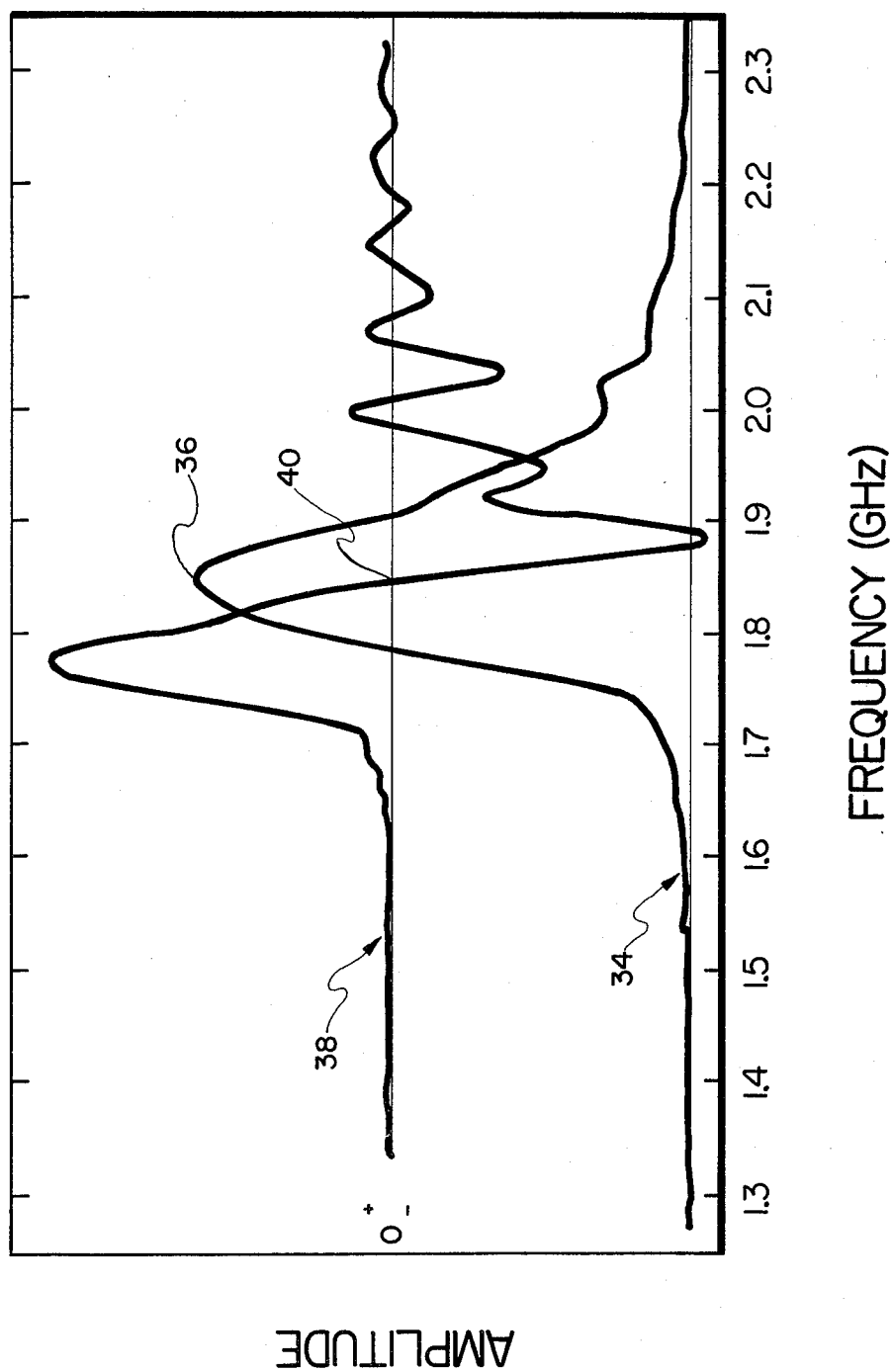
FIG. 4 is the signal (and its derivative) near the cut-off frequency for a ¾ inch diameter waveguide filled with 99.5% acetone, balance water.
Figure 5:
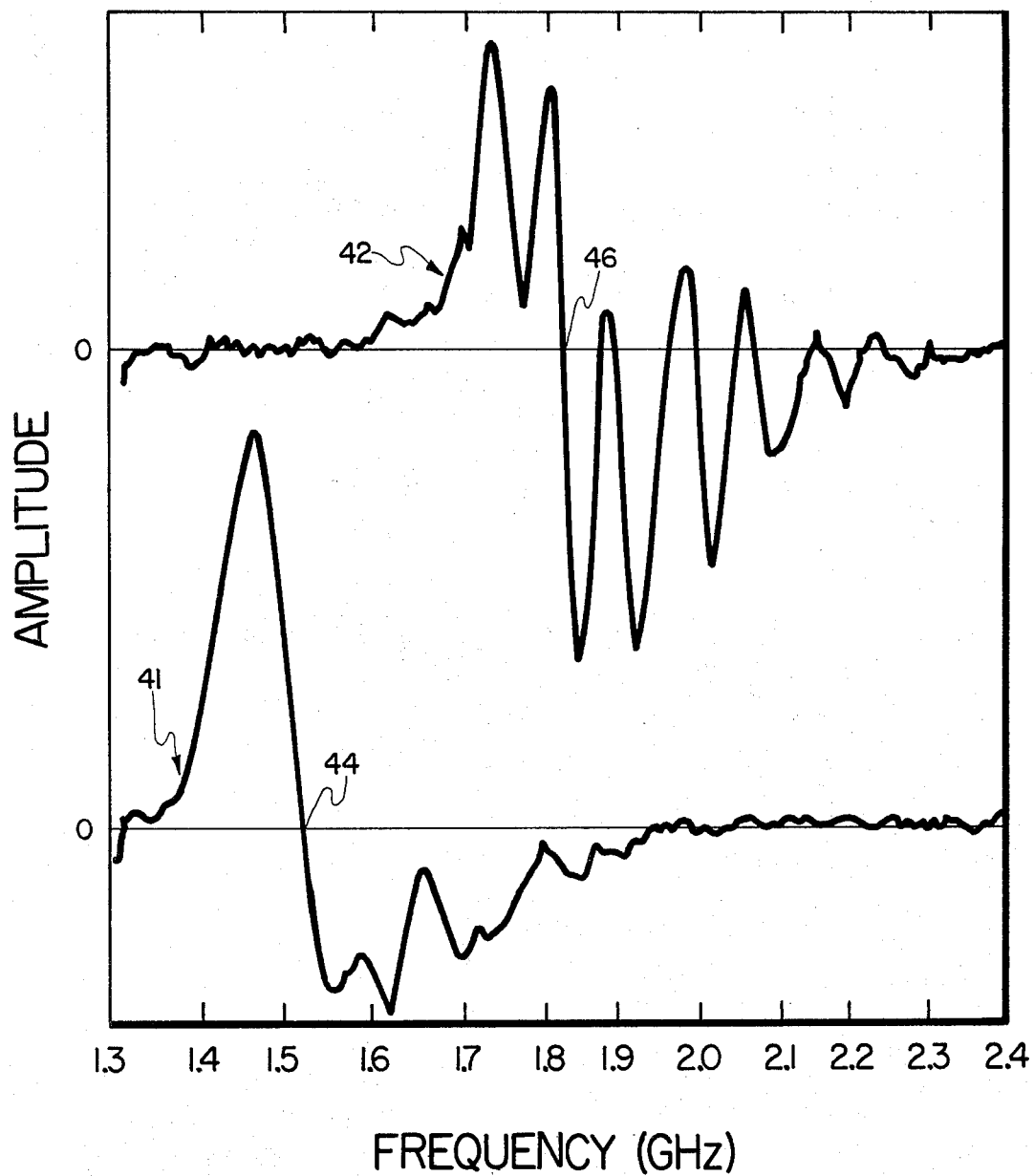
FIG. 5 is the derivative of the signal near the cut-off frequency for a ¾ inch diameter waveguide filled with a 46.7% coal slurry (curve 41) and with a 61.5% coal slurry (curve 42)
Figure 6:
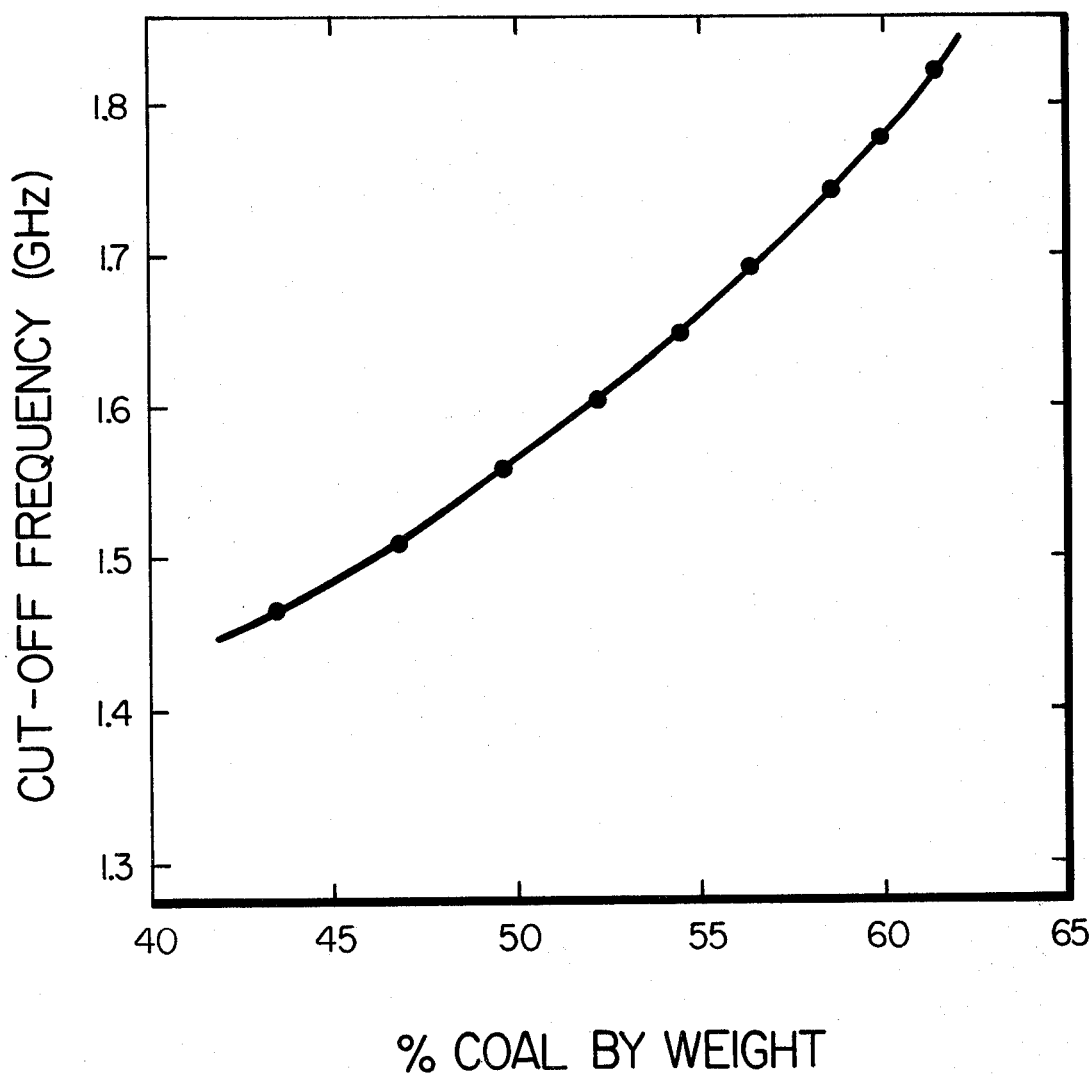
FIG. 6 is a plot of cut-off frequency vs % coal for a coal slurry in the ¾ inch diameter waveguide.

FIGS. 4-6 illustrate a method used to calibrate the waveguide to measure the composition of mixtures using the second embodiment. Curve 34 in FIG. 4 is the signal received by detecting probe 12 when transmitting probe 10 is swept at frequencies from 1.3 to 2.3 GHz. This curve was obtained using the apparatus shown in FIG. 2 with the ¾ inch diameter waveguide 2 filled with a mixture of 99.5% acetone and 0.5% water. The maximum signal 36 corresponds to a frequency slightly above the cut-off frequency of the lowest frequency mode of microwave propagation in the waveguide. This corresponds to the TE$_{11}$ mode for circular waveguide 2.

Curve 38 in FIG. 4 is the first derivative of the signal shown in curve 34. Maximum signal 36 corresponds to zero point 40 of the derivative of the detector signal with respect to frequency. This derivative is easily obtained by slowly scanning the microwave frequency while simultaneously adding a small sinusoidal frequency modulation on to a slowly changing frequency. There are two advantages to using the derivative at the frequency of the maximum signal:

(1) the steepness of the curve is greatest and less subject to artifacts, and;
(2) the detector sensitivity is greatest at this point.

In order to calibrate a waveguide to measure the fraction of acetone in water, a series of curves such as curve 38 is obtained for various compositions of acetone and water. The composition of an unknown mixture of acetone and water can then be determined by measuring its cut-off frequency and comparing it to the experimentally determined relationship.

FIGS. 5-6 illustrate the calibration of a waveguide for measuring the composition of a coal slurry. A coal slurry containing 46.7% coal and balance water is pumped through waveguide 2. Lock-in amplifier 26 is set so that the derivative of the signal from detector probe 12 is plotted as a function of frequency, resulting in curve 41 of FIG. 5. The process is repeated for a 61.5% coal slurry (curve 42) and for any other composition within the desired range of the meter. The zero crossings 44, 46 of the derivatives are then used as a convenient measure of the cut-off frequency.

Finally, the cut-off frequencies obtained are plotted against the percent coal as shown in FIG. 6. Waveguide 2 can now be used to determine the composition of unknown coal slurries by measuring the cut-off frequency of the unknown slurry and comparing it to the relationship shown in FIG. 6. This method and meter can be used in a similar fashion to determine the composition of any fluid mixture having a dielectric constant which varies with composition.

In a third embodiment of the invention, the meter can be used to measure the flow rate of a heterogeneous flowing system such as a coal slurry. In such systems, there are local variations in the composition of the mixture and the microwave measuring system shown in FIG. 2 will indicate these variations as fluctuations in the measured frequency characteristics as previously described. By using a lock-in amplifier to hold the frequency to the point of the maximum signal, the frequency fluctuations can be translated to voltage fluctuations.

By using two detector probes, it is possible to monitor fluctuations at two different points along the waveguide. This permits, for example, a maximum signal at the upstream detector probe to be related to the same signal at a downstream detector probe at a later time. The time difference, $\tau$, is then directly related to the velocity of the mixture, assuming that axial mixing is negligible.

The cross correlation function, $C_{1,2}(\tau)$ for upstream signal $S_1(t)$ and downstream signals $S_2(t)$, is given by:

$$C_{1,2}(\tau) = \int_0^t S_1(t) S_2(t \pm \tau) dt \qquad (4)$$

Although cross correlation can be accomplished using a waveguide with a single transmitter probe and two spaced detector probes, matching the microwave characteristics can be a problem. This can be overcome by using two separate source lock-in amplifier circuits, each corresponding to the one shown in FIG. 2, or by rapid multiplexing the circuit of FIG. 2 to operate on either pair of antenna 10 and 12. As shown in FIG. 1, two pair 6, 8 of transmitter and receiver probes 10, 12 spaced distance 48 from each other are provided for each source lock-in amplifier circuit. Thus, even if the measured characteristic frequencies (determined by a long term average) are different, the changes with composition will still correlate. The use of two pairs of probes offers the additional advantage that the best separation 48 between detector probes can be selected for the desired range of flow rates.

An oscilloscope can be used to monitor the lock-in amplifier outputs of both detectors. In this way, if there are large fluctuations, they are immediately apparent and the time difference is readily approximated. Determination of the correlation time can be automated by recording the time dependence of both signals on a data acquisition system and cross-correlating them by the digitized form of the correlation function:

$$C_{1,2}(m) = \sum_{n=0}^{N/2} S_1(n) S_2(n + m) \qquad (5)$$

where:
N = the number of points in the array,
n = the index of each array,
m corresponds to the index of the correlation,
$S_1(n)$ = the upstream signal, and
$S_2(n+m)$ = the downstream signal.

The appropriate correlation time, $\tau$, corresponds to the maximum of $C_{1,2}(m)$, defined at index m', and is equal to m' times the time increment between data points. The linear flow velocity, V, can then be calculated by dividing the distance separating the detector probes (48 in FIG. 1) by the correlation time.

Figure 7:
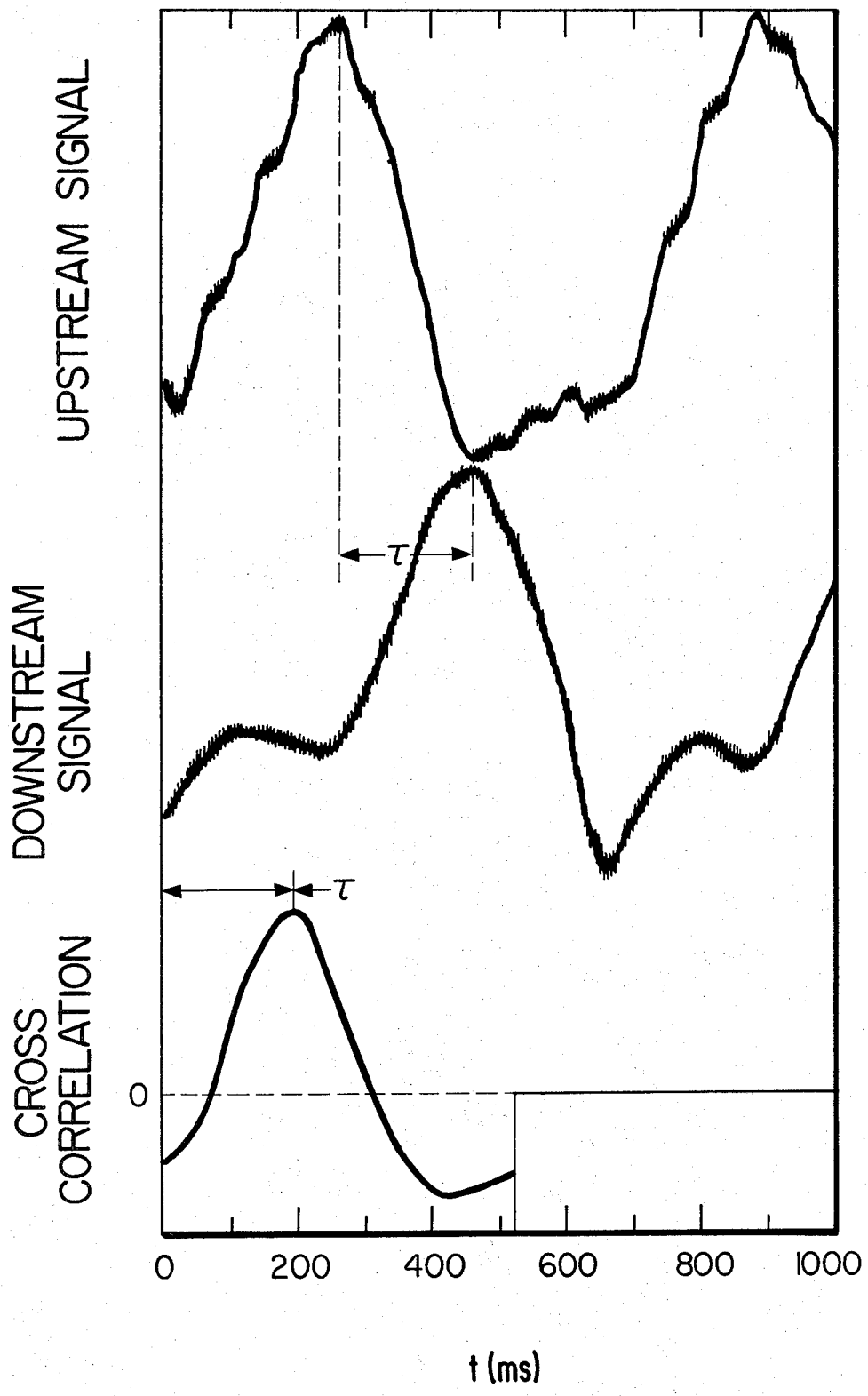
FIG. 7 is a plot of the fluctuations in cut-off frequency from two detecting probes separated by 10.71 cm, and their cross correlation.

Fluctuations in the cut-off frequency from two coal slurry monitoring channels are shown in FIG. 7. The detector probes were separated by 10.71 cm in a ¾ inch diameter pipe. The cross correlation (given by Equation 5), is shown in the lower portion of the figure, and it gives a time delay, $\tau$, of 205 ms. For a 10.71 cm probe separation, this results in an apparent linear flow velocity of 52 cm per second. This linear velocity can readily be converted to volume velocity and the meter calibrated empirically to measure actual volume velocity.

Numerous variations and modifications can be made without departing from the invention. For example, microwave energy can be coupled into the waveguide using various coupling antenna designs or iris windows. Rectangular rather than circular waveguides can be used. The detector probe can be movable so that the length of the propagating wave, $\lambda_g$, can be measured at a fixed frequency rather than varying the frequency to determine the frequency of the propagating wave for a fixed wavelength. Accordingly, it should be clearly understood that the form of the invention described above and shown in the drawings is illustrative only and is not intended to limit the scope of the invention.

What is claimed is:

1. A meter comprising:
   a waveguide through which a substance to be measured can flow;
   means for positioning said waveguide in series with a conduit through which said substance can flow into said waveguide;
   a transmitter microwave probe in said waveguide;
   a detector microwave probe in said waveguide located a predetermined distance from said transmitter microwave probe;
   a microwave generator coupled to said transmitter microwave probe;
   an amplifier coupled to said detector microwave probe for amplifying signals;
   a diode detector coupled to said amplifier for rectifying signals; and
   a lock-in amplifier coupled to said detector for determining a frequency characteristic of microwave propagation within said waveguide.

2. The meter as claimed in claim 1, including means for varying the frequency of transmitted microwaves, said means for varying being coupled to said generator, and wherein said frequency characteristic comprises the cut-off frequency of said waveguide.

3. A meter comprising:
   a waveguide for containing a substance to be measured;
   a first pair of transmitter and detector microwave probes comprising a first transmitter probe and a first detector probe separated from each other along said waveguide;
   a second pair of transmitter and detector microwave probes comprising a second transmitter probe and a second detector probe separated from each other along said waveguide, said first and second pairs of probes being separated from each other a predetermined distance;
   generating means coupled to said first and to said second transmitter probes for generating and transmitting microwaves to them;
   means coupled to said generating means for varying the frequency of transmitted microwaves;
   detector means coupled to said first and to said second detector probes for detecting microwaves received by them;
   electronic means coupled to said detector means for determining the cut-off frequency of the waveguide between said transmitter and said detector probes of said first pair, and the cut-off frequency of the waveguide between said transmitter and detector probes of said second pair; and
   means for cross correlating the cut-off frequencies obtained for the waveguides between said first and said second pair of probes.

4. A method of measuring an ingredient in a mixture of ingredients, comprising the steps of:
   providing a waveguide for propagating microwaves and for containing said mixture;
   determining a relationship between the quantity of said ingredients in said mixture and a frequency characteristic of said mixture in said waveguide by:
     placing samples of said mixture having known quantities of said ingredients in said waveguide;
     propagating microwaves in said waveguide;
     varying the frequency of said microwaves;
     detecting said microwaves after they have propagated in said waveguide; and
     determining a frequency characteristic of said waveguide with each of said samples; placing said mixture to be measured in said waveguide;
   propagating microwaves in said waveguide containing said mixture to be measured;
   varying the frequency of said microwaves;
   detecting said microwaves after they have propagated in said waveguide;
   determining a frequency characteristic of said waveguide with said mixture to be measured contained therein; and
   comparing said frequency characteristic of said mixture with said relationship, whereby the quantity of said ingredient in said mixture is measured.

5. The method as claimed in claim 4 wherein said frequency characteristic comprises the frequency of a microwave propagating in said waveguide.

6. The method as claimed in claim 4 wherein said frequency characteristic comprises the wavelength of a microwave propagating in said waveguide.

7. The method as claimed in claim 4 wherein said frequency characteristic comprises the cut-off frequency of said waveguide.

8. A method of measuring the flow rate of a heterogeneous mixture of ingredients, comprising the steps of:
   providing a waveguide through which the mixture to be measured can flow;
   propagating microwaves in a first section of said waveguide while said mixture is flowing in said waveguide;
   detecting said microwaves after they have propagated in said first section of said waveguide;
   determining a time dependent characteristic frequency of said first section of said waveguide containing said mixture;
   propagating microwaves in a second section of said waveguide while said mixture is flowing in said waveguide, said second section being located a predetermined distance from said first section;
   detecting said microwaves after they have propagated in said second section of said waveguide;

determining a time dependent characteristic frequency of said second section of said waveguide containing said mixture;

cross correlating the time dependent characteristic frequencies obtained for said first and said second sections of said waveguide, whereby the flow rate of said mixture is measured.

9. A method of measuring an ingredient in a mixture of ingredients, comprising the steps of:

providing a waveguide for containing said mixture;

determining a relationship between the quantity of said ingredients in said mixture and a frequency characteristic of said mixture in said waveguide by:

placing samples of said mixture having known quantities of said ingredient in said waveguide;

propagating microwaves in said waveguide;

detecting said microwaves after they have propagated in said waveguide; and determining a frequency characteristic of said waveguide with each of said samples; placing said mixture to be measured in said waveguide;

propagating microwaves in a first portion of said waveguide containing said mixture to be measured;

detecting said microwaves after they have propagated in said first portion of said waveguide;

determining a frequency characteristic of said first portion of said waveguide with said mixture to be measured contained therein;

propagating microwaves in a second portion of said waveguide which is spaced a predetermined distance from said portion;

detecting said microwaves after they have propagated in said second portion of said waveguide;

determining a frequency characteristic of said second portion of said waveguide; and cross-correlating said frequency characteristic obtained for said first and second portion of said waveguide, whereby the flow rate of said mixture is measured, and comparing said frequency characteristic of said mixture with said relationship, whereby the quantity of said ingredient in said mixture is measured.

10. A meter comprising:

a waveguide for containing a substance to be measured;

propagating means coupled to said waveguide for propagating microwaves in said waveguide;

means for varying the frequency of said microwaves, said means for varying being coupled to said propagating means;

detecting means for detecting said microwaves after they have propagated down said waveguide, said detecting means being coupled to said waveguide and spaced from said propagating means; and a lock-in amplifier coupled to said detecting means for receiving a signal from said detecting means and measuring the power of said signal at predetermined frequencies.

11. A meter comprising:

a waveguide for containing a substance to be measured, said waveguide having a first waveguide portion and a second waveguide portion;

propagating means coupled to said waveguide for propagating microwaves in said waveguide;

means for varying the frequency of said microwaves, said means for varying being coupled to said propagating means;

a first and a second detecting means for detecting microwaves after they have propagated down said first and said second waveguide portions, respectively, said first and second detecting means being coupled to said waveguide and spaced from said propgating means;

a first and a second electronic means coupled to said first and second detecting means for determining the cut-off frequency of said first and second waveguide portions, respectively; and a means for cross-correlating the cut-off frequencies of said first and second waveguide portions.

* * * * *